US006867353B2

(12) United States Patent
Kim et al.

(10) Patent No.: US 6,867,353 B2
(45) Date of Patent: Mar. 15, 2005

(54) PRODUCTION METHOD OF RECOMBINANT ROTAVIRUS STRUCTURAL PROTEINS AND VACCINE COMPOSITION

(75) Inventors: Won-Yong Kim, Seoul (KR); In-Sik Chung, Suwon-si (KR); Youn-Hyung Lee, Suwon-si (KR); Hong-Joong Kim, Seoul (KR)

(73) Assignee: Exploregen Inc., Seoul (KR)

( * ) Notice: Subject to any disclaimer, the term of this patent is extended or adjusted under 35 U.S.C. 154(b) by 115 days.

(21) Appl. No.: 10/203,523

(22) PCT Filed: Feb. 12, 2001

(86) PCT No.: PCT/KR01/00206

§ 371 (c)(1),
(2), (4) Date: Sep. 30, 2002

(87) PCT Pub. No.: WO01/59070

PCT Pub. Date: Aug. 16, 2001

(65) Prior Publication Data

US 2003/0175303 A1 Sep. 18, 2003

(30) Foreign Application Priority Data

Feb. 12, 2000 (KR) .......................................... 2000-6694

(51) Int. Cl.$^7$ .......................... A01H 1/00; A61K 39/12; C07H 21/04; C07K 14/005; C12N 5/14

(52) U.S. Cl. .................. 800/317.4; 435/69.1; 435/69.3; 435/468; 435/411; 435/419; 435/320.1; 530/350; 536/23.72; 800/278; 800/288; 800/295; 424/186.1; 424/215.1

(58) Field of Search ............................... 435/69.1, 69.3, 435/468, 411, 419, 320.1; 530/350; 536/23.72; 800/278, 288, 295; 424/186.1, 215.1

(56) References Cited

PUBLICATIONS

GenEmbl Accession No. U04741, Palombo et al. Sequences of VP6 genes of human rotavirus strain RV3 and its vaccine derivative. J. Gen. Virol., vol. 75 (Pt 9), 1994, p. 2415–2419.*

Palombo et al., J. Gen. Virol., 75 (Pt 9), 1994, p. 2415–2419.*

Mary. K. Estes et al, "Rotavirus Gene Structure and Function," Microbiological Reviews, pp. 410–449, 1989.

Gwenola Tosser et al, "Expression of the Major Capsid Protein VP6 of Group C rotavirus and Synthesis of Chimeric Single–Shelled Particles by Using Recombinant Baculoviruses," Journal of Virology, vol. 66, No. 10, pp. 5825–5831, 1992.

U. Desselberger et al, "The Rotavirus Genome," Current Topics in Microbiology and Immunology, vol. 185, pp. 31–66, 1994.

B. Verdaguer et al, "Isolation and expression in transgenic tobacco and rice plants, of the cassava vein mosaic virus (CVMV) promoter," Plant Molecular Biology, vol. 31, pp. 1129–1139, 1996.

J. Paszkowski et al, "Direct gene transfer to plants," The EMBO Journal, vol. 3, No. 12, pp. 2717–2722, 1984.

G. An et al, "New cloning vehicles for transformation of higher plants," The EMBO Journal, vol. 4, No. 2, pp. 277–284, 1985.

Fraley et al, "A Simple and General Method for Transferring Genes into Plants," Science, vol. 227, pp. 1229–1231, 1985.

"Withdrawal of Rotavirus Vaccine Recommendation," Morbidity and Mortality Weekly Report (MMWR), vol. 48, No. 43, pp. 1007–1008, 1999.

Roger I. Glass et al, "Rotavirus Vaccines: Success by Reassortment?" Science, vol. 265, pp. 1389–1391, 1994.

Mary K. Estes et al, "Synthesis and Imunogenicity of the Rotavirus Major Capsid Antigen Using a Baculovirus Expression System," Journal of Virology, vol. 61, No. 5, pp. 1488–1494, 1987.

Robert E. Smith et al, "Cloning and expression of the major inner cpasid protein of SA–11 simian rotavirus in *Escherichia coli*," Gene, vol. 79, pp. 239–248, 1989.

Neil R. Blacklow, M.D. et al, "Viral Gastroenteritis," The New England Journal of Medicine, vol. 325, No. 4, pp. 252–264, 1991.

U. K. Laemmli, "Cleavage of Structural Proteins during the Assembly of the Head of Bacteriophage T4," Nature, vol. 227, pp. 680–685, 1970.

V. Chizhikov et al, "A four–nucleotide translation enhancer in the 3'–terminal consensus sequence of the nonpolyadenylated mRNAs of rotavirus," RNA, vol. 6, No. 6, pp. 814–825, 2000 (abstract only).

M. Nejmeddine et al, "Rotavirus spike protein VP4 is present at the plasma membrane and is associated with microtubules in infected cells," J. Virol., vol. 74, No. 7, pp. 3313–3320, 2000 (abstract only).

(List continued on next page.)

*Primary Examiner*—Phuong T. Bui
(74) *Attorney, Agent, or Firm*—Burns, Doane, Swecker & Mathis, L.L.P.

(57) ABSTRACT

The present invention relates to a method for producing recombinant rotavirus structural proteins by culturing a transformed plant cell, and to a vaccine composition comprising the same as an effective component. More specifically, the method comprises the steps of preparing the expression vector comprising cDNA fragments encoding rotavirus structural proteins; transforming a plant cell with the expression vector; and recovering the vaccine composition, including rotavirus antigens, from the cell culture. The method for producing the recombinant rotavirus structural proteins is advantageous in that higher yields of more than 0.3 mg/L are obtained, as well as a lower cost and a lower contamination hazard than those of eukaryotic expression systems such as baculovirus and animal cell. Furthermore, the method can be used to produce a edible vaccine. The invention also proves that the rotavirus structural protein can be produced with a high aspect rotary vessel reactor.

1 Claim, 7 Drawing Sheets

OTHER PUBLICATIONS

G. J. O'Brien et al, "Rotavirus VP6 expressed by PVX vectors in Nicotiana benthamiana coats PVX rods and also assembles into viruslike particles," Virology, vol. 270, No. 2, pp. 444–453, 2000 (abstract only).
A. L. Loy et al, "Immune response to rotavirus VP4 expressed in an attenuated strain of Shigella flexneri," FEMS Immunol Med. Microbiol., vol. 25, No. 3, pp. 283–288, 1999 (abstract only).
I. Petitpas et al, "Crystallization and preliminary X–Ray analysis of rotavirus protein VP6," J. Virol., vol. 72, No. 9, pp. 7615–7619, 1988 (abstract only).
G. Tosser et al, "Expression of the major capsid protein VP6 of group C rotavirus and synthesis of chimeric single–shelled particles by using recombinant baculoviruses," J. Virol, vol. 66, No. 10, pp. 5825–5831, 1992 (abstract only).

* cited by examiner

US 6,867,353 B2

PRODUCTION METHOD OF RECOMBINANT ROTAVIRUS STRUCTURAL PROTEINS AND VACCINE COMPOSITION

FIELD OF THE INVENTION

The present invention relates to a method for producing the structural proteins of the recombinant rotavirus by culturing a transformed plant cell, and the vaccine composition comprising such proteins as an effective component. More particularly, the method comprises the steps of producing the recombinant expression plasmid including the gene encoding the human rotavirus structural protein, transforming the plant cell with the expression plasmid, cultivating the plant cell, and obtaining the vaccine composition including rotavirus antigen recovered from the culture solution.

BACKGROUND OF THE INVENTION

In 1973, Bishop discovered the Rotavirus in Australia firstly. The rotavirus is a double stranded RNA virus and belongs to the Reoviridae family. The rotavirus causes acute gastroenteritis in infant and is infected via fecal-oral route after an incubation period of about 1 to 3 weeks. The disease is severe in 6 to 24 week infants, but is mild or asymptomatic in neonate or most of adults. Thus, the acute infectious diarrhea by the rotavirus is a main cause of the death in the world. Moreover, it is estimated that about a million of patients are died of the infectious diarrhea by the rotavirus in the developing countries [see reference: Blacklow, N. R. & Greenburg, H. B., (1991) Viral gastroentertitis *N. Engl. J. Med.*, 325:152–164, 1991]. Therefore, world health organization (WHO) considered more efficient suppression and prevention for the infection by the rotavirus the first research subject [see reference: Glass, R. I et al., (1994) Rotavirus vaccines: success by reassortment *Science* 265–1389–1391].

The rotavirus is usually globular shape and is named after the outer and inner shells or double-shelled capsid structure of the same. The outer capsid is about 70 nm, and inner capsid is about 55 nm in diameter, respectively. The double-shelled capsid of the rotavirus surrounds the core including the inner protein shell and genome. The genome of the rotavirus consists of double stranded RNA segments encoding at least 11 rotavirus proteins. The inner capsid includes VP6 and VP2 proteins. VP4 and VP7 lie in outer side of the double-shelled capsid and constitute the outer capsid. Depending upon the antigenicity of VP6 which is a group-specific antigen, the rotavirus is divided into seven groups, A to G. VP2 protein is related to the synthesis of RNA. Group A rotavirus is further divided into the G-type (glycoprotein type) on the basis of the glycoprotein VP7, and P-type (protease-cleaved protein) on the basis of the VP4 which are associated with an important immunogenicity of the virus by forming a neutralizing antibody [see references: Estes M. K., et al., (1987) Synthesis and immunogenicity of the rotavirus major capsid antigen using a baculovirus expression system, *J. Virol.* 61:1488–1494; Estes M. K. & Cohen J., (1989) Rotavirus gene structure and function. *Microbiol. Rev.* 53:410—419; Desselberger U & McCrae M. A., (1994) The rotavirus genome. *Curr. Microbiol. Immuno.* 185:31–66].

The methods to treat the acute diarrhea disease caused by the rotavirus were restricted to administer non-specific physical strength supplements such as water and electrolyte. Thus, the vaccine as an effective therapeutic agent has been required for completely preventing the human from the all serum-type of human rotavirus. As an attempt, a live vaccine of attenuated human rotavirus, animal rotavirus such as cow, or reassortants comprised of RNA segments derived from different serotypes human and animal rotavirus have been used. As a result of such study, Wyeth Laboratories, a manufacturing company of vaccines, reported first rotavirus vaccine, RotaShield (trademark). The vaccine was produced by reassorting rotavirus of Rhesus monkey and human rotavirus of 3 serum types and was firstly approved by Food and Drug Administration (FDA) in the world in 1998. However, the FDA's approval to the vaccine was tentatively canceled in 1999, because of the side effects such as intussusception [*MMWR Morb. Mortal Wkly. Rep.*, (1999) 5;48(43):1007].

Apart from the above, a study that the part of rotavirus is produced on a large scale through genetic recombinant technology and is used as a subunit vaccine is proceeding. In this point, many researchers have studied the expression of the rotavirus capsid proteins in *E. coli* expression system, baculrovirus expression system or mammalian expression system [Smith R. E. et al., (1989) Cloning and expression of the major inner capsid protein of SA-11 simian rotavirus in *E. coli. Gene* 79:239–248; Tosser G. et al., (1992) Expression of the major capsid protein VP6 of group C rotavirus and synthesis of chimeric single-shelled particles by using recombinant baculoviruses. *J. Virol.* 66:5825–5831; Ito H. et al., (1997) Expression of the major inner capsid protein, VP6, of avian rotavirus in mammalian cells. *Vet. Microbiol.* 49:257–265].

However, it is difficult to produce the rotavirus on a large scale by cell culture, because the rotavirus is infected through the mucus cell. That is, because it is difficult to produce the virus protein particles similar to natural virus in prokaryotic expression systems such as *E. coli* expression system, the particle does not elicit antigenecity. In view of contamination hazard during culture process, purification problem, high cost and low yield, the mammalian expression system is not satisfactory.

Also, most of disease caused by rotavirus is commonly occurred in developing countries which are deficient in sanitary facilities and vaccine supplement. Even if technical success of the method for producing the virus structural proteins in other cells and the vaccine composition comprising the proteins is possible, long time and many studies are required for commercializing the method in view of high production cost and sale price. On the other hand, if the rotavirus structural protein can be produced by using plant, especially edible plant and can be used for producing the vaccine, it is very economical in view of low production cost, no purification process, and efficiency in transport and storage.

Therefore, the present inventors found that rotavirus structural proteins capable of inducing the mucus and systemic immune response can be produced in the plant cell which is transformed with plant expression vector including rotavirus capsid gene, and then the plant cell is cultured under the suitable condition. Also, the vaccine composition comprising the rotavirus structural proteins can be obtained.

Figure 1A:
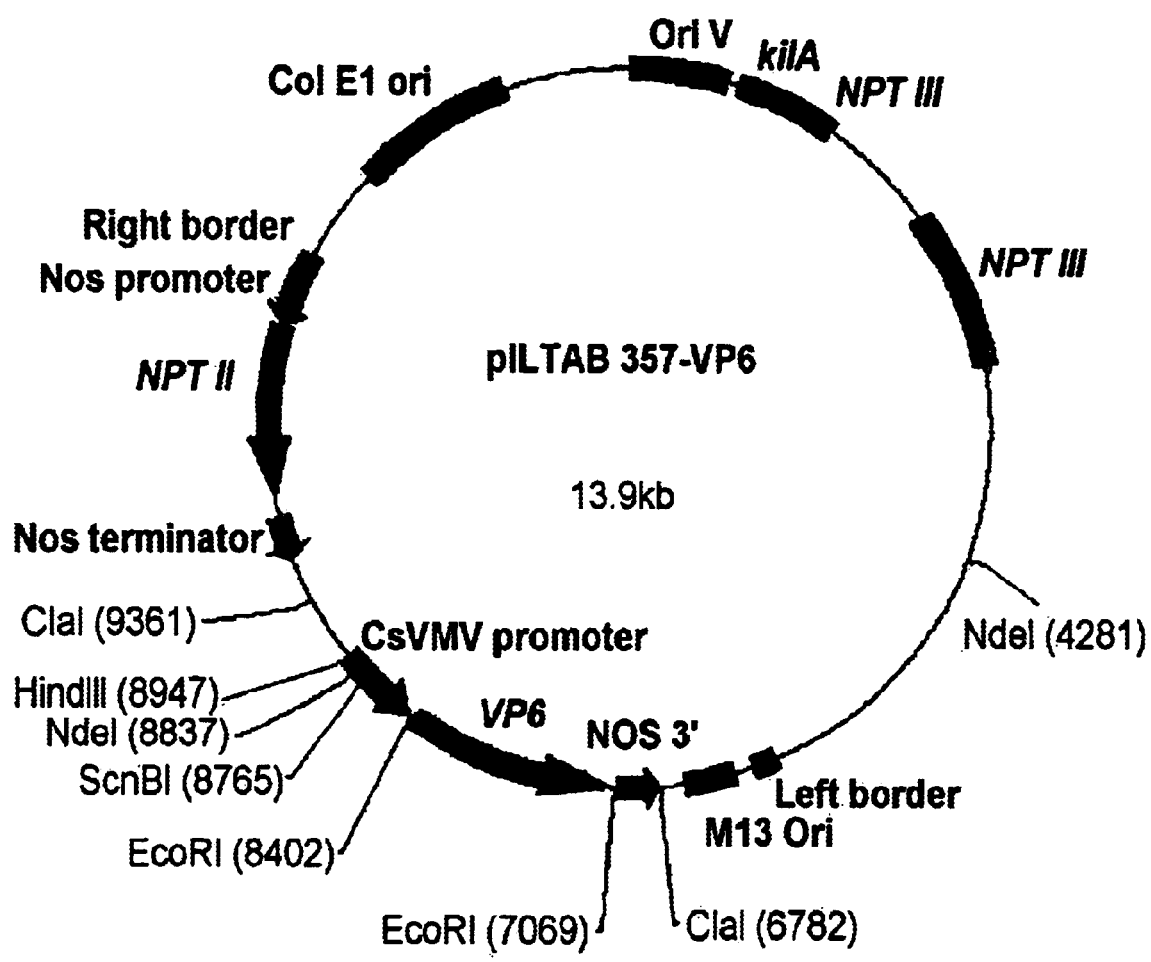
FIGS. 1a–1d are cleavage maps showing the structure of binary vector used for transforming a plant cell, pILTAB357-VP6, pILTAB357-VP2, pILTAB357-VP4 and pILTAB357-VP7, CsVMV promoter: Cassava vein mosaic virus promoter NOS promoter: nopalin synthase promoter NOS 3': nopalin synthase transcription terminator region NPT II: neomycin phosphotransferase II gene

M: marker of molecular weight,

1: intracellular fraction of the normal cell,

2: medium fraction of the normal cell,

3: intracellular fraction of the transformed tomato cell,

4: medium fraction of the transformed tomato cell,

Other features and advantages of the invention will be apparent from the following detailed description, and from the examples.

DETAILED DESCRIPTION OF THE INVENTION

The present invention provides the structural proteins of the recombinant human rotavirus obtained by culturing transformed plant cells, and the vaccine composition comprising such proteins as an effective component.

The method for producing antigenic recombinant human rotavirus structural protein in plant cell comprising the steps of:

1) preparing the recombinant expression plasmid by inserting cDNA fragment encoding human rotavirus structural protein into the expression plasmid for transforming plant, which comprises the promoter regulating plant-specific expression and selection marker;

2) introducing the recombinant expression plasmid of step 1 into plant cell;

3) inducing formation of callus from the plant cell which is introduced with the recombinant expression plasmid of step 2;

4) regenerating the callus of step 3 to the whole plants; and 5) recovering the recombinant human rotavirus structural protein in the plants of step 4.

The wide range of sources (e.g., human rotavirus and animal rotavirus such as cow) are available for the gene encoding rotavirus structural protein of step 1, as long as the gene encodes the rotavirus capsid protein. And, it is preferable to use the gene encoding inner capsid protein VP6, the gene encoding inner capsid protein VP2, the gene encoding outer capsid protein VP4, and the gene encoding outer capsid protein VP7. The rotavirus gene of the interest can be obtained by amplifying the gene from the feces of the subject hating rotavirus-related disease with the known polymerase chain reaction (PCR). In a desired embodiment of the present invention, VP6 gene fragment can be available by excising the gene from the plasmid pGEM-VP6 (KCTC 8984P). In another embodiment of the invention, cDNA fragment encoding VP2, VP4, and VP7 serotype G1, VP7 serotype G2, VP7 serotype G3 and VP7 serotype G4 can be used by isolating and amplifying the cDNA fragment from the faces of the subject having rotavirus-related disease.

Also, recombinant plasmid expressing the cDNA fragment encoding the human rotavirus structural protein of the interest of step 1 can be constructed from the known plant expression vector as a basic vector. The binary vector, cointegration vector, or a general vector which is designed not to include T-DNA region but to be capable of being expressed in plant can be also available.

In the present invention, the examples of the desired binary vector include final binary vectors, for example, pILTAB357-VP6, pILTAB357-VP2, pILTAB357-VP4, pILTAB357-VP7, which are prepared by inserting the cDNA fragment encoding each human rotavirus structural proteins, VP6, VP2, VP4 or VP7 into binary vectors comprising left border of T-DNA relating lo infection of a foreign gene and right border of T-DNA for transforming a plant cell, cassava vein mosaic virus promoter between the left border and the right border, nopalin synthase promoter, transcription termination region of nopalin synthase, and selection marker for selecting transformants.

As the promoter regulating the plant-specific expression, all the known expression vectors maximally expressing the recombinant proteins in plant cell can be used, and the promoter includes ubiquitin promoter, actin promoter, PG promoter or endosperm-specific promoter other than the cassava vein mosaic virus promoter.

In the transformation of the plant cell in step 2, when the binary vector or the cointegration vector is used, the plant cell transformation method mediated by agrobacterium will be employed. In such case, *Agrobacterium tumefaciens* or *Agrobacterium rhizogenes* can be used.

In the desired embodiment of the present invention, the final binary vector can be introduced into *Agrobacterium tumefaciens* via the known triparental mating. The tirparental mating is a method of introducing the plasmid having the gene of interest to the *agrobacterium* by coculturing *E. coli* including helper plasmid for conjugation. *E. coli* including the recombinant plasmid having the gene of interest and *Agrobacterium* for transforming the plant cell all together. More specifically, the parent *E. coli* used for triparent mating can be *E. coli* having the pILTAB357-VP6, and tomato seedling cotyledon can be transformed with the *agrobacterium* transformed by the tirparental mating.

In case of transforming the monocotyledon plant with the vector which does not include T-DNA region, polyethylene glycol-mediated uptake, electroporation, or microparticle bombardment can be used and transformation using single DNA and simultaneous transformation using multiple DNA also can be used.

The transformed cell can be redifferentiated by using the standard technologies known to those skilled in the art. The plant cell which may be transformed by the above method includes dicotyledon plant such as lettuce, Chinese cabbage, radish, potato, and tomato, etc. and monocotyledon plant such as rice, barley, and banana, etc. Especially, in case of producing the human rotavirus structural protein and the particle similar to the same by transforming edible plant, uptake of the transformed plant itself can induce directly the immune response, so it can be effectively used as a edible vaccine.

The selection marker to select the transformed plant cell is usually antibiotic resistant gene, but is not limited to the same. For examples, herbicide resistant gene, metabolism-related gene, luminous gene, green fluorescence protein (GFP), β-glucuronidase (GUS) gene, β-galactosidase (GAL) gene can be used as selection marker. Specifically, neomycin phosphotransferase II (NPTII) gene, hygromycin phosphotransferase gene, phosphynotricin acetyltransferase gene, or dihydrofolate reductase gene can be used.

Meanwhile, the transformed plant cell of the present invention can be cultured by employing microgravity culture in High Aspect Rotating-Wall Vessel as well as the suspension culture. When the High Aspect Rotating-Wall Vessel is used, the cell growth rate is very slow compared to the general suspension culture method, because the lag phase is longer in order to fit the circumstance of the mimic microgravity. However, it is found that rotavirus protein yield per cell weight in the rotary reactor is similar to that in the suspension culture.

Also, the present invention provides rotavirus-like particle which can be made by folding the human rotavirus structural proteins of the invention, VP2, VP6, VP4 and VP7. Herein, 'rotavirus-like particle' is intended to mean the antigenic particle obtained from an assembly of at least a capsid protein, or self-assembly of the same.

Furthermore, the present invention provides a vaccine composition useful for treatment and prevention from rotavirus-related disease comprising the human rotavirus structural protein of the present invention as an effective component. More specifically, the vaccine composition comprises at least one selected form the group consisting of VP4, G1 serotype VP7, G2 serotype VP7, G3 serotype VP7, and G4 serotype VP7, or preferably comprises VP2 and VP6.

To prepare for the vaccine composition, the human rotavirus structural proteins produced by the transformed plant cell can be isolated and purified from the cell culture by using the known purification method, but in case of transforming by using edible plant cell, it is more preferable to prepare the rotavirus structural proteins using plant cell itself, the part of redifferentiated transformed plant or the extract of plant without purification process in view of the production cost and process management.

The vaccine useful for treatment and prevention for rotavirus-related disease can be administered orally or parenterally, and can be used in the usual form of drug.

Namely, the human rotavirus vaccine composition can be prepared by containing optionally a pharmaceutically acceptable diluent or excipient such as filler, extender, binding agent, wetting agent, integrant, and surfactant. The solid preparation for oral administration includes tablet, pill, powder, grannule, capsule, and can be prepared by mixing at least one of the excipient such as starch, calcium carbonate, sucrose, lactose, and gelatin with rotavirus vaccine composition. Also, lubricant such as magnesium stearate, talc as well as simple excipients can be used. The liquid preparation for oral administration can contain suspension, liquid drug, emulsion, and syrup, and include many excipient (e.g., wetting agent, sweetening agent, fragrant, preserving agent) other than commonly used simple diluents such as water, liquid and paraffin. The preparation for parenteral administration contains sterilized solution, non-aqueous solvent, suspension solvent, is emulsifier, freeze-drying agent or suppository. The non-aqueous solvent or suspension solvent can include propylene glycol, polyethylene glycol, vegetable oil such as olive oil, injectable ester such as ethyloleate. The basic material of suppository includes witepsol, macrogol, tween 61, cacao paper, laurin paper, glycerogelatin.

However, because most of rotavirus vaccine are administered to infant, especially 2 to 24 month-old infant, it is preferable to be administered as soon as possible before firstly exposed to the rotavirus, and the dosage form of the vaccine is more preferably oral preparation in liquid, injectable preparation, or suppository in order to easily administer to the infant.

As described below, the present invention will be more specifically illustrated by examples of the expression system that cDNA encoding the recombinant human rotavirus structural protein is expressed in the transformed tomato cell in culture systems, and the expression system that the High Aspect Rotating-Wall Vessel designed by NASA is employed for optimally culturing the recombinant human rotavirus structural proteins. However, modification or change of the method can be used, and thus the method does not limited to the following definite working examples.

Preparation of Vector Including cDNA Fragment Encoding Rotavirus Structural Protein The gene cloning technology used herein can be easily performed by employing the method known to those skilled in the art. Such methods are well described in the following references such as Sambrook et al., 1989, Molecular Cloning A Laboratory Manual, Cold Spring Harbor Laboratory, N.Y.; and Ausubel et al., 1989, Current Protocols in Molecular Biology, Greene Publishing Associate and Wiley Interscience, N.Y.

A kind of binary vector used for transforming dicotyledon plant, especially tomato, is very various, and most of binary vectors can be available in international depository authority, for example, Center for the Application of Molecular Biology to International Agriculture (CAMBIA, GPO Box 3200, Canberra ACT2601, Australia). Basic binary vector which is variously modified to include selection marker, promoter, transcription terminator region in left border and right border region of transferred gene is used.

In the examples of the present invention, pGEM-VP6 (KCTC 0944BP) including cDNA encoding human rotavirus VP6 protein was used in order to constitute the binary vector. Also, the plasmids including cDNA fragment encoding human rotavirus VP2 of SEQ ID NO:1, cDNA fragment encoding human rotavirus VP4 of SEQ ID NO:2, cDNA fragment encoding human rotavirus VP6 of SEQ ID NO:3, and cDNA fragment encoding human rotavirus VP7 of SEQ ID NO:4 to SEQ ID NO:7 having different serotype, respectively, were used. However, the vector suitable for the present invention is not limited to the above plasmids, and all range of the vectors which efficiently express the genes can be used. In the examples of the present invention, the plasmid transforming plant cell was constructed by inserting cDNA fragment to the cloning site of known plasmid, pILTAB357 (Scripps Research Institute, U.S.A.; Verdaguer et al, Isolation and expression in transgenic tobacco and nice plants, of the cassava vein mosaic virus promoter, *Plant Molecular Biology* 31: 1129–1139, 1996), using CsVMV promoter in T-DNA region of pILTAB357 and inserting neomycin phosphotransferase II (NPTII) gene as a selection marker (see FIGS. 1*a*–1*d*).

Transformation Procedure

Transformation can be performed according to the method known to those skilled in the art which the present invention pertains to. The plant can be transformed via agrobacterium-mediated transformation which is illustrated in Paszkowsky et al., EMBO J 3:2717–2722 (1984). For example, agrobacterium-mediated transformation for the tomato is described in An et al., EMBO J 4–227–288 (1985). The transformation of monocotyledon plant can be achieved by directly implanting the gene into plasma via PEG or electroporation, or by introducing the gene into the callus tissue via particle bombardment. The transformed cell can be redifferentiated to the whole plant via the standard method known to those skilled in the art. The host cell for transformation can be usually *Agrobacterium tumefaciens,* and *Agrobacterium tumefaciens* strain LBA4404 which is well-known in the art was used in the desired embodiment of the present invention.

The binary vector of the, present invention was introduced to *Agrobacterium tumefaciens* via triparental mating. In such case, for example, *E. coli* MM294 including pILTAB357-VP6 which has the inserted cDNA fragment encoding human rotavirus VP6 protein was used as parent strain. Then, cotyledon excised from tomato (*Lycopersicon esclentum* Mill) seedling was transformed with recombinant *Agrobacterium tumefaciens* LBA 4404.

Transformant Culture Procedure To culture the transformed tomato cells, suspension culture and High Aspect Rotating-Wall Vessel were used. To do this, sterilized tomato (*Lycopersicon esclentum* Mill) seed was inoculated on MS (Murashige and Skoog) medium, and was germinated, and then co-cultured with suspension culture solution containing *Agrobacterium tumefaciens* LBA 4404 including recombinant expression plasmid, and cultured successively. Also, to determine the culture system that can optimally produce recombinant rotavirus structural proteins, VP6, VP2, VP4 and VP7, the transformed tomato cell was cultured in a microgravity model system with High Aspect Rotating-Wall vessel designed by NASA.

The Expression of the Recombinant Rotavirus Structural Proteins

The transformed tomato cell was established from the selected kanamycin-resistant callus, and was maintained in liquid medium added by kanamycin 200 mg/L for 3 months. The degree of gene expression was analyzed using the transformed tomato cell on two weeks after culture and normal tomato cell. Recombinant rotavirus structural proteins, VP6, VP2, VP4 and VP7 could be detected in the transformed tomato cell by western blotting.

For example, recombinant rotavirus protein VP6 is largely in intracellular fraction, and has molecular weight of about 44 kDa. VP2 has molecular weight of 94 kDa, and VP4 has a molecular weight of 87 kDa and VP7 has a molecular weight of 34 kDa. Such measured molecular weight of the proteins is almost consistent with those derived from the nucleotide sequencing. Recombinant rotavirus proteins, VP6, VP2, VP4 and VP7 were not detected in the non-transformed cell or fraction. The fact means that VP6, VP2, VP4 and VP7 were expressed from pILTAB357-VP6, pILTAB357-VP2, pILTAB357-VP4 and pILTAB357-VP7 transformed in the tomato cell.

The invention will be further described in the following examples, which are not intended to limit the scope of the invention.

EXAMPLE 1

Construction of Binary Vector for Transformation

The fragment produced by digesting pGEM-VP6 (KCTC 0944BP) including gene encoding human rotavirus VP6 protein with restriction enzyme EcoRI was inserted into the EcoRI restriction site of plasmid pILTAB357 (Scripps Research Institute, U.S.A.) to prepare recombinant plasmid pILTAB357-VP6 of 13.94 kb. FIG. 1*a* shows cleavage map of the pILTAB357-VP6. In the pILTAB357-VP6, the CsVMV promoter inserted between the left border and the right border of binary vector for transforming plant cell, pILTAB357 was used as a promoter for regulating the transcription of VP6 gene [Verdaguer B., et al., (1996) Isolation and expression in transgenic tobacco and rice plants, of the cassava vein mosaic virus (CsVMV) promoter. *Plant Mol. Biol.* 31:1129–1139], and neomycin phosphotransferase II (NPTII) was inserted as a marker for selecting the transformant in the growth medium containing kanamycin (FIG. 1*a*). By using restriction map and DNA sequencing, the location of VP6 gene in recombinant plasmid, pILTAB357-VP6, and whether reading frame of the VP6 was correctly inserted were identified. The prepared binary vector was introduced to *Agrobacterium tumefaciens* LBA 4404 (Cat. No. 18313–015, GibcoBRL, U.S.A.) via triparental mating [Ainsworth C. et al., (1996) *Techniques in Plant Molecular Biology,* Wye, UK: Wye College]. In the triparental mating, *E. coli* MM294 (KCCM 70079) including pILTAB357-VP6 was used as parent strain. Cotyledon cut from tomato (*Lycopersicon esclentum* Mill) was transformed with the recombinant *Agrobacterium tumefaciens* LBA 4404 according to agrobacterium-mediated leaf disc transformation [Horsch R. B. et al., Science 227: 1229–1231, 1985].

EXAMPLE 2

Transformation Procedure and Establishment of Suspension Culture for the Transformed Cell Tomato (*Lycopersicon esculentum* Mill) seed was immersed in 70% ethanol solution for 1 minute, sterilized with 1.2% sodium hypochloride (NaOCl) solution for 30 minutes, and then, was washed with sterilized distilled water many times. The sterilized seed was inoculated on MS medium [sucrose 30 g/l, 2,4-D (2,4-dichlorophenoxyacetic acid) 2 mg/l, kinetin 0.2 mg/l, timentin 150 mg/l, pH 5.7] containing agar 8 g/L. The seed applied on Magenta box was germinated in culture room in light cycle of 12 hours at 27° C. After about two weeks, germinated sterilized young seedling was used for transformation experiment. Cotyledon excised from the seedling was immersed in suspension culture of recombinant *agrobacterium tumefaciens* LBA 4404 including pILTAB357-VP6 for 3 minutes, and then extra microorganism was removed with filter paper. Then, explants were cultured with *agrobacterim tumefaciens* LBA 4404 on solid MS medium containing agar 8 g for 3 days. The resultant explants were transferred onto MS medium containing kanamycin B 200 mg/L and timentin 150 mg/l. The explants were incubated in culture room at 27° C. in light cycle of 12 hours for 4 weeks in order to induce callus. The induced callus was cut and then was maintained and amplified by passage culture at 4 weeks interval. The callus resistant to kanamycin was selected and transferred onto the liquid medium containing kanamycin 200 mg/L but not agar, and then, was cultured in suspension.

The transformed plant cell was cultured in suspension medium containing kanamycin B 200 mg/L in rotary shaking flask at 27° C., 100 rpm, and was maintained and amplified by passage culture at 3 weeks interval. The callus of normal tomato cell was induced as control according to all the process described above, except the process of transformation of agrobacterium, and cultured in suspension under the same conditions.

EXAMPLE 3

Suspension Culture and Gene Expression Anaylsis

1) Suspension Culture of the Transformed Plant Cell and Isolation of VP6

The transformed tomato cell was cultured at 27° C., 100 rpm in shaking flask containing MS liquid media 50 mg/L including kanamycin 200 mg/L. During the culture time, the cultured cell was collected and analyzed for the cell growth and expression of the recombinant protein at a regular interval.

The culture was centrifugated at 3,000 rpm for 5 minutes to separate the cell, and supernatant was used for analyzing extracellular recombinant protein. Cell fraction was freezed with liquid nitrogen, and then was grinded with mortar and pestle with adding protein extraction solution [Tris-HCl (pH 7.5) 50 mM, ethylenediaminetetraacetic acid (EDTA) 2 mM, ethylenebis (oxyethylenenitrilo) tetraacetic acid (EGTA) 0.5 mM, phenylmethylsulfonyl fluoride (PMSF) 1 mM, 1% Triton X-100]. Then the resultant was sonicated in the centrifugation tube at 4° C. for 5 minutes 3 times. The cell extract was centrifuged at 14,000 rpm at 4° C., for 15 minutes to remove cell debris, and supernatant was used for analyzing the intracellular recombinant protein. Unless especially defined, the mixture of intracellular fraction and extracellular fraction was used for analysis of protein production in total.

2) Gene Expression Analysis

The production amount of the recombinant rotavirus VP6 protein was measured by western blotting by using fusion VP6 protein of 44.5 kDa expressed in *E. coli* as control. The fusion VP6 protein has a molecular weight of 44.5 kDa. The fusion VP6 protein was expressed in *E. coli* using pET-15b (Novagen, U.S.A.) designed to express VP6 protein in *E. coli* and used by purifying with His-Bind kit (Novagen, U.S.A.). Polyhistidine tag sequence linked to cleavage site of thrombin is fused in N-terminal of fusion VP6 protein.

According to Laemmli's method, SDS-PAGE electrophoresis was performed on the protein sample [Laemmli U.K. (1970) Cleavage of structural proteins during the assembly of the head of bacteriophage T4. *Nature* 227:680–685]. After electrophoresis, the resultant proteins were transferred onto nitrocellulose membrane and then, were combined with anti-rotravirus polyclonal antibody (Chung-Ang University, Seoul, Korea) obtained from Guinea pig, and were detected by rabbit anti-Guinea pig immunoglobulin G (Kirkegaard & Perry Laboratories, U.S.A.). After washing nitrocellulose membrane with buffer solution, the resultant was colored with BM purple AP substrate solution (Boehringer Mannheim, U.S.A.) and quenched by adding distilled water.

Recombinant rotavirus protein VP6 was largely in intracellular fraction of the transformed plant and had molecular weight of about 44.5 kDa, which is consistent with that of VP6 expressed in *E. coli*. This shows that the transformed plant cell of the present invention expressed successfully rotavirus protein VP6.

The production amount of recombinant rotavirus proteins VP6 was 0.33 mg/L on 18 day after culture.

EXAMPLE 4

Microgravity Culture

To test microgravity, culture solution of the transformed tomato cell wasa filled up in High Aspect Rotating-Wall vessel (HARV, Synthecon, Houston, Tex.) with the capacity of 10 ml to produce recombinant rotavirus VP6 and cultured for 18 days. The production amount of recombinant rotavirus VP6 in HARV was 0.13–0.15 mg/L.

EXAMPLE 5

Figure 1B:
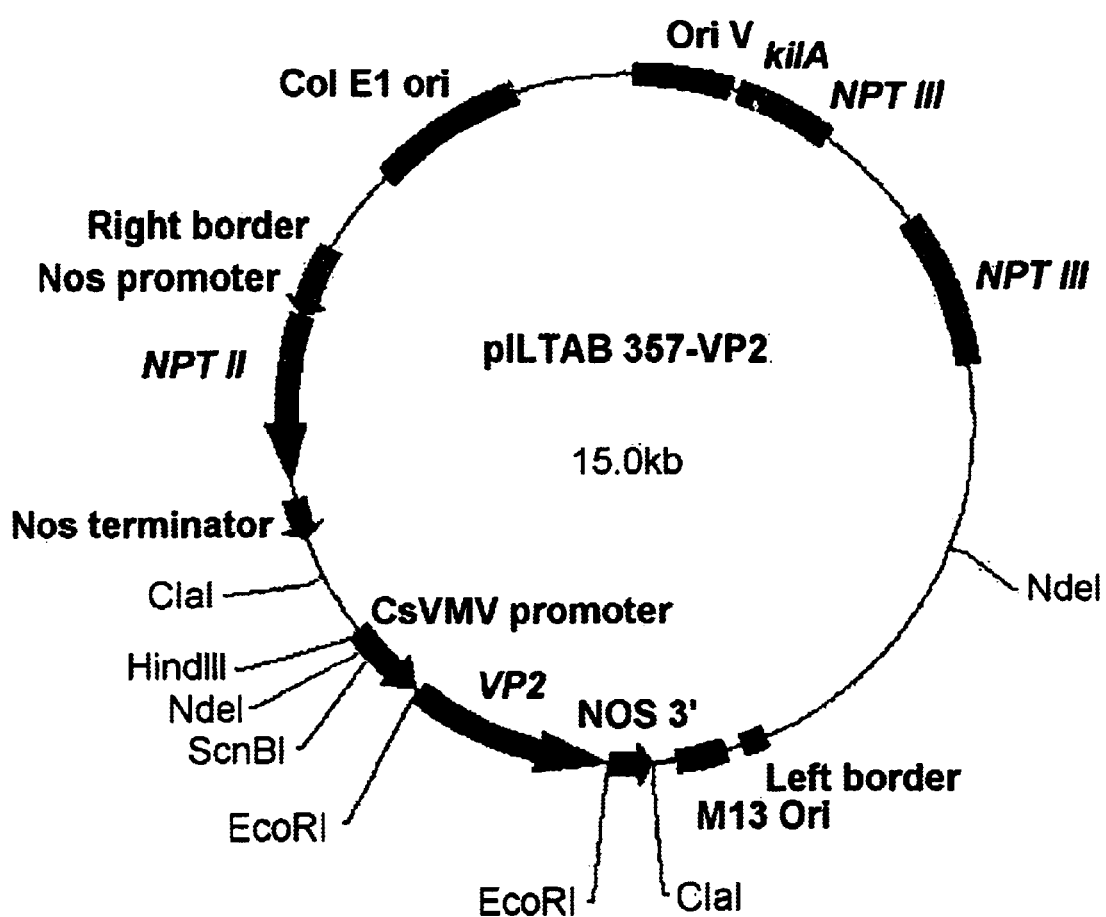
Figure 2A:
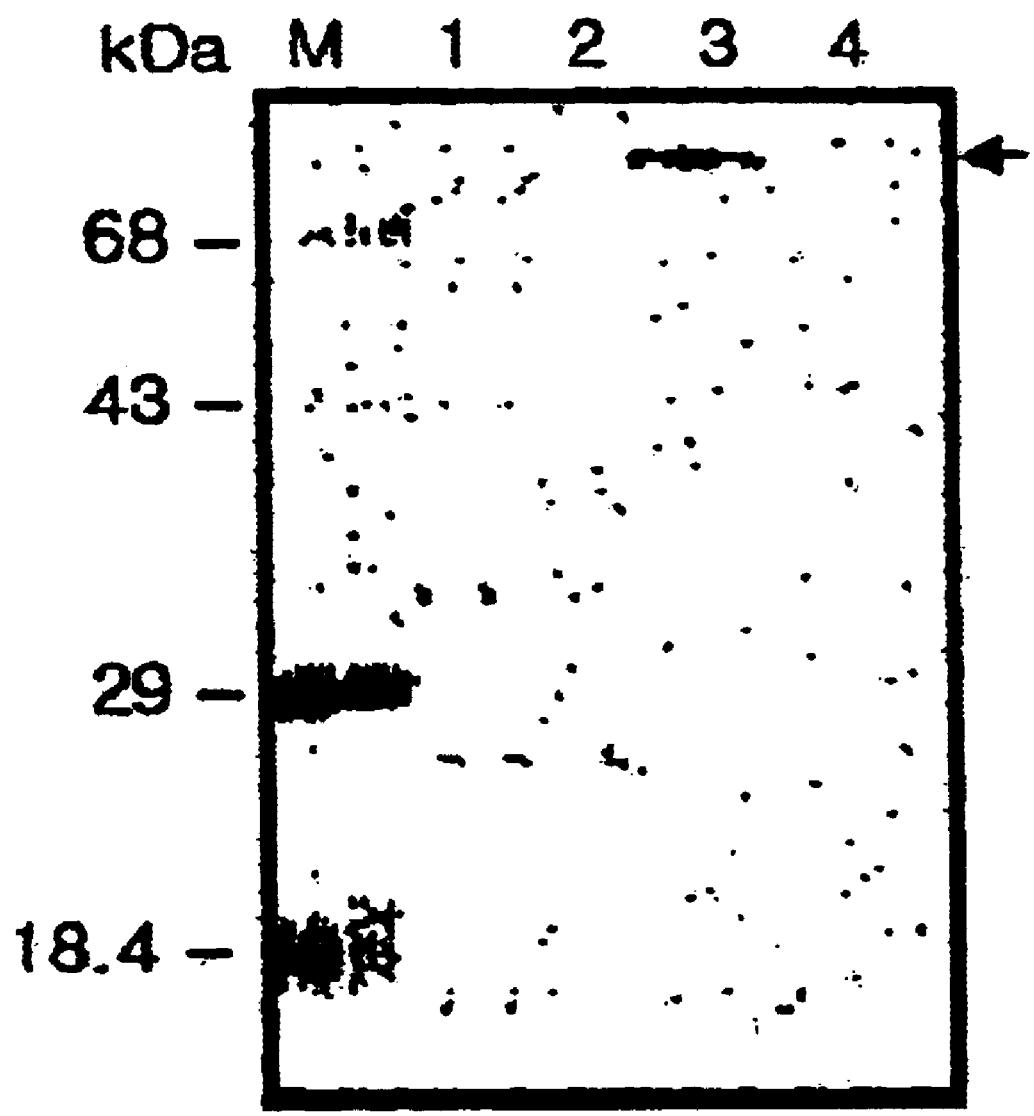
FIGS. 2a–2c are the result of western blotting of normal and transformed tomato cell. The arrows show recombinant rotavirus proteins, VP2, VP4 and VP7 respectively.

Except that recombinant plasmid, pILTAB357-VP2 of 15.0 kb prepared by using pGEM-VP2 (KCTC 0947BP) including cDNA fragment of SEQ ID NO:1 encoding human rotavirus protein VP2, was used, instead of pGEM-VP6 (KCTC 0944BP) including cDNA fragment encoding human rotavirus protein VP6, cotyledon excised from tomato seedling was transformed with *Agrobacterium tumefaciens* to which introduced binary vector pILTAB357-VP2 according to the same method of Examples 1–3. Then, transformed tomato cell was cultured in suspension. The recombinant rotavirus protein VP2 was isolated, and was analyzed with western blotting in order to identify that the transformed cell expresses rotavirus protein VP2 successfully (FIG. 2a).

pGEM-VP2 including cDNA fragment encoding VP2 derived from human rotavirus was deposited on Feb. 8, 2001 to Korea Collection for Type Culture (KCTC) under Budapest treaty on the international recognition of the deposit of microorganism, and was acceded KCTC 0947BP as a deposit number. The cleavage map of recombinant plasmid, pILTAB357-VP2 was shown in FIG. 1b.

EXAMPLE 6

Figure 1C:
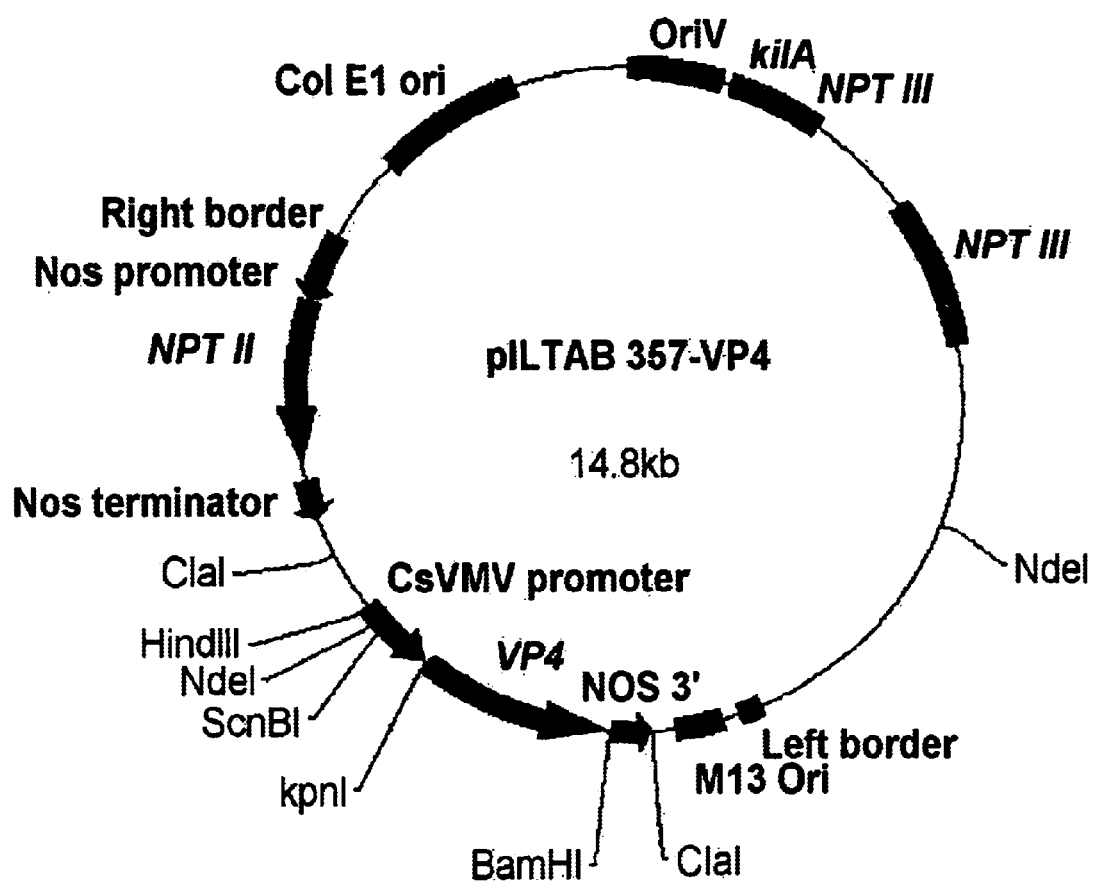
Figure 2B:
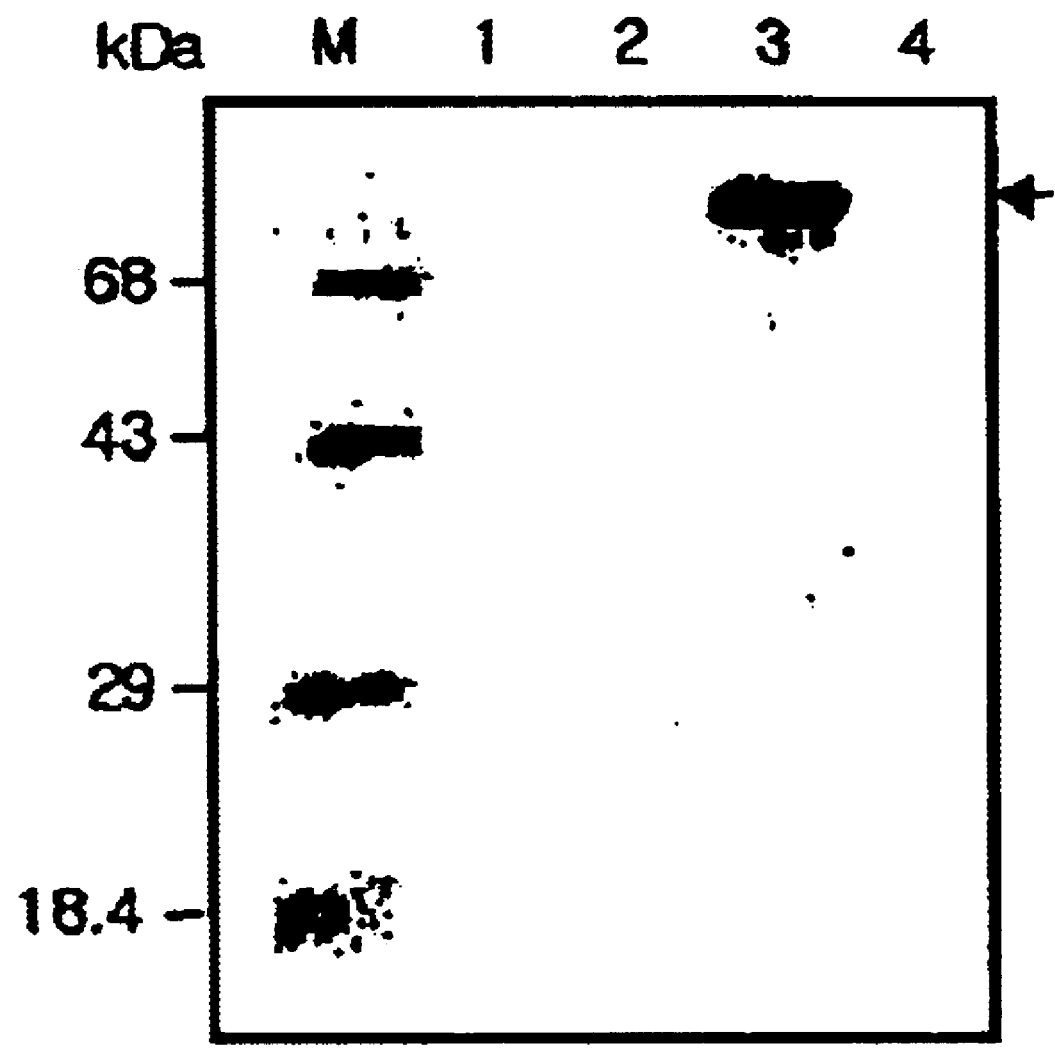

Except that recombinant plasmid, pILTAB357-VP4 of 14.8 kb prepared by using pGEM-VP4 (KCTC 0945BP) including cDNA fragment of SEQ ID NO:2 encoding human rotavirus protein VP4, was used, instead of pGEM-VP6 (KCTC 0944BP) including cDNA fragment encoding human rotavirus protein VP6, cotyledon excised from tomato seedling was transformed with *Agrobacterium tumefaciens* to which introduced binary vector pILTAB357-VP4 according to the same method of Examples 1–3. Then, transformed tomato cell was cultured in suspension. The recombinant rotavirus protein VP4 was isolated, and was analyzed with western blotting in order to identify that the transformed cell expresses rotavirus protein VP4 successfully (FIG. 2b).

pGEM-VP4 including cDNA fragment encoding VP4 derived from human rotavirus was deposited on Feb. 8, 2001 to Korea Collection for Type Culture (KCTC) under Budapest treaty on the international recognition of the deposit of microorganism, and was acceded KCTC 0945BP as a deposit number. The cleavage map of recombinant plasmid, pILTAB357-VP4 was shown in FIG. 1c.

EXAMPLE 7

Figure 1D:
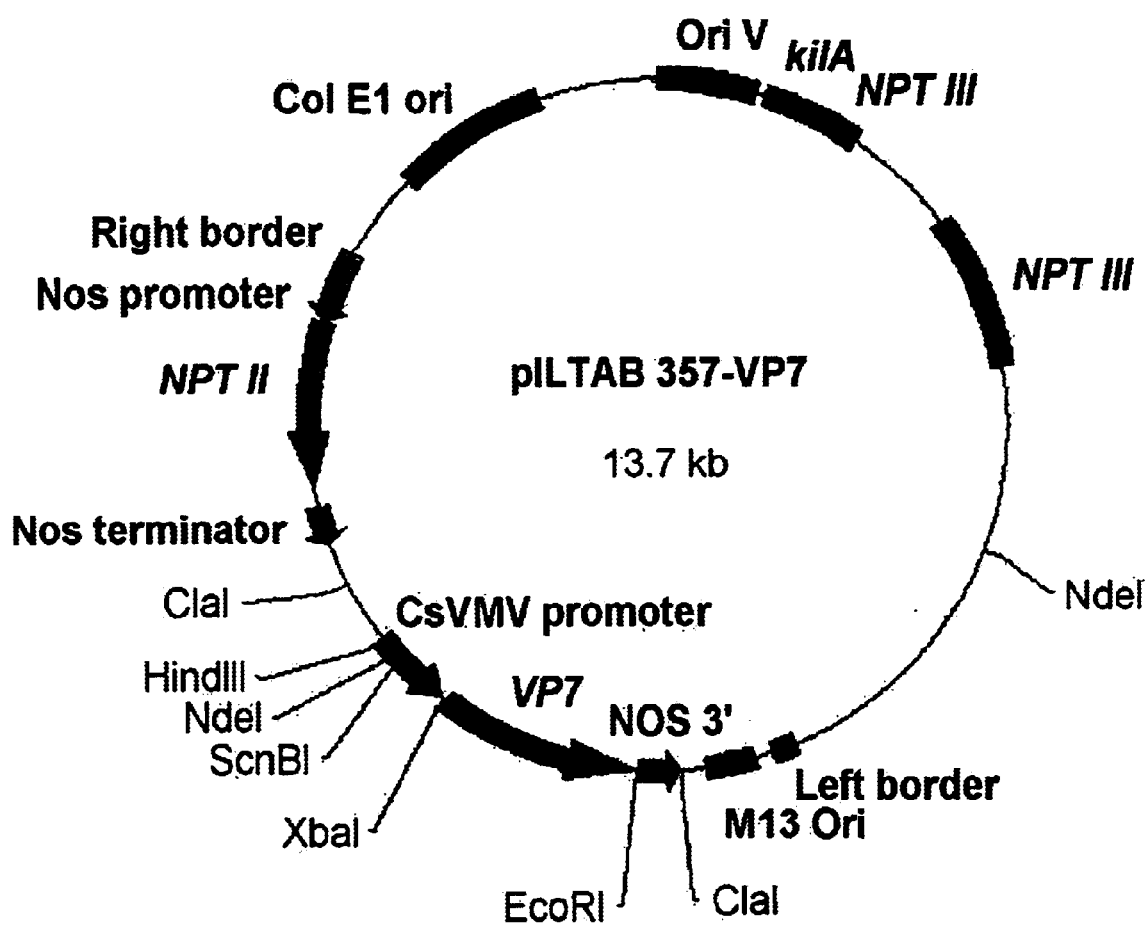
Figure 2C:
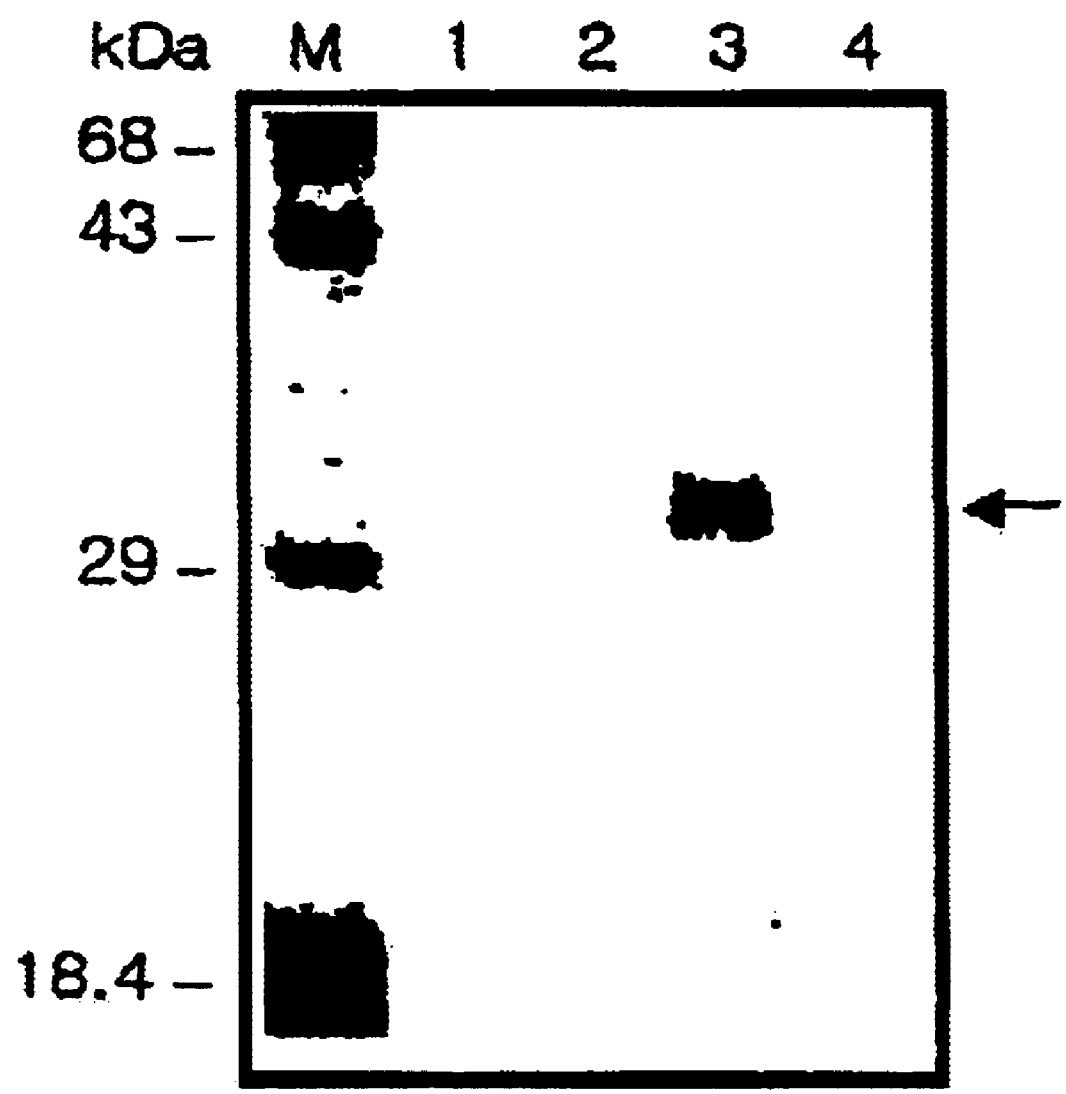

Except that recombinant plasmid, pILTAB357-VP7 of 13.7 kb prepared by using pGEM-VP7 (KCTC 0946BP) including cDNA fragment of SEQ ID NO:4 encoding human rotavirus protein VP7 serotype G1, was used, instead of pGEM-VP6 (KCTC 0944BP) including cDNA fragment encoding human rotavirus protein VP6, cotyledon excised from tomato seedling was transformed with *Agrobacterium tumefaciens* to which introduced binary vector pILTAB357-VP7 according to the same method of Examples 1–3. Then, transformed tomato cell was cultured in suspension. The recombinant rotavirus protein VP7 was isolated, and was analyzed with western blotting in order to identify that the transformed cell expresses rotavirus protein VP7 serotype G1 successfully (FIG. 2c).

pGEM-VP7 including cDNA fragment encoding VP7 having serotype G1 derived from human rotavirus was deposited on Feb. 8, 2001 to Korea Collection for Type Culture (KCTC) under Budapest treaty on the international recognition of the deposit of microorganism, and was acceded KCTC 0946BP as a deposit number. The cleavage map of recombinant plasmid, pILTAB357-VP7 was shown in FIG. 1d.

EXAMPLE 8

The pCR2.1-VP7 (KCTC 0948BP) including cDNA fragment of SEQ ID NO:5 encoding human rotavirus protein VP7 serotype G2 was used, instead of pGEM-VP7(KCTC 0946BP) including cDNA fragment encoding human rotavirus protein VP7 serotype G1 as described in Example 7. It was confirmed that the transformed cell expressed rotavirus protein VP7 serotype G2 successfully by working according to the same method as example 7.

The pCR2.1-VP7 including cDNA fragment encoding VP7 serotype G2 derived from human rotavirus was deposited on Feb. 8, 2001 to Korea Collection for Type Culture (KCTC) under Budapest treaty on the international recognition of the deposit of microorganism, and was acceded KCTC 0948BP as a deposit Number.

EXAMPLE 9

The pCR2.1-VP7 (KCTC 0949BP) including cDNA fragment of SEQ ID NO:6 encoding human rotavirus protein VP7 serotype G3 was used, instead of pGEM-VP7 (KCTC 0946BP) including cDNA fragment encoding human rotavirus protein VP7 having G1 serotype as described in Example 7. It was confirmed that the transformed cell expressed rotavirus protein VP7 serotype G3 successfully by working according to the same method as example 7.

The pCR2.1-VP7 including cDNA fragment encoding VP7 serotype G3 derived from human rotavirus was deposited on Feb. 8, 2001 to Korea Collection for Type Culture (KCTC) under Budapest treaty on the international recognition of the deposit of microorganism, and was acceded KCTC 0949BP as a deposit Number.

EXAMPLE 10

The pCR2.1-VP7 (KCTC 0950BP) including cDNA fragment of SEQ ID NO:7 encoding human rotavirus protein VP7 serotype G4 was used, instead of pGEM-VP7 (KCTC 0946BP) including cDNA fragment encoding human rotavirus protein VP7 having G1 serotype as described in Example 7. It was confirmed that the transformed cell expressed rotavirus protein VP7 serotype G4 successfully by working according to the same method as example 7.

The pCR2.1-VP7 including cDNA fragment encoding VP7 serotype G4 derived from human rotavirus was deposited on Feb. 8, 2001 to Korea Collection for Type Culture (KCTC) under Budapest treaty on the international recognition of the deposit of microorganism, and was acceded KCTC 0950BP as a deposit Number.

INDUSTRIAL APPLICABILITY

According to the genetic recombination technology of the present invention, the method for producing rotavirus structural proteins in plant cell on a large scale and vaccine composition comprising the proteins as an effective component has advantages in low production cost and no need to purification. Also, when the protein is produced from edible plant, it is possible to use the protein as edible vaccine or oral vaccine by preparing vaccine comprising the isolated virus structural proteins and pharmaceutically acceptable additive, or by taking the plant itself directly. In particular, when it is important to induce mucus immune response such as rotavirus, the oral vaccine contributes desired mucous and systemic immune response. Thus, the protein can be used for vaccine composition useful for treatment and prevention from rotavirus-related disease. In addition, the method of the present invention is easy and efficient in aspect of transport and storages compared to other culture system.

What is claimed is:

1. A transformed tomato comprising cDNA fragment encoding human rotavirus structural protein having the sequence represented by SEQ ID NO:3 encoding VP6 derived from human rotavirus.

* * * * *

SEQUENCE LISTING

<160> NUMBER OF SEQ ID NOS: 7

<210> SEQ ID NO 1
<211> LENGTH: 2729
<212> TYPE: DNA
<213> ORGANISM: Human rotavirus

<400> SEQUENCE: 1

```
tcctattaaa ggttcaatgg cgtacaggaa gcgtggagct aaacgtgaag acttactaca      60
acaaaatgaa cgtctgcaag aaaaagaaat tgaaaataat accgacgtaa ccatggaaaa     120
tagaaataaa aataaaaata acaatagaaa gcagcaatta tctgacaaag tgttatcacg     180
aaaagaggaa ataataactg atgtgcaaga tgacattaaa atagctgatg aggtcaaaaa     240
atcatcaaaa gaagagtcga aacagttact tgaaatatta aaaacgaaag aagatcatca     300 gaagaagta cagtacgaaa ttttacaaaa aacaatacca acttttgaac caaaagaatc      360
aattctgaaa aaattagaag atataagacc agaacaagct aagaagcaaa tgaaattgtt     420
tagaatattt gaaccaagac aattaccaat ctatcgagca aacggtgaga aagaattaag     480
gaatagatgg tactggaaat taaaaaagga tacactacca gacggagatt atgacgtacg     540
agaatatttt ttaaatttat atgatcaaat actgatagaa atgccagatt atttattgtt     600
aaaagatatg gctgtagaaa ataaaaactc cagggatgct ggtaaggttg tagattctga     660
gactgcaagt atttgtgatg ctatatttca agatgaggag acagagggag ttattagaag     720
atttatagca gatatgagac aacaagttca ggctgataga aatattgtca attatccatc     780
aattttacat ccaattgatt atgcatttaa tgaatatttt ctaaaccatc aattagttga     840
accattgaat aacgaaatta tttttaatta tataccagaa agaataagga atgatgtcaa     900 ttatatttg aatatggata tgaatttacc atcaacagca agatatatta gaccaaatct     960
```

-continued

```
attgcaagat agactgaatt tacatgataa ttttgagtca ttatgggaca caataactac    1020
atcaaattac atattggcaa gatcagtcgt gcctgatttg aaggaaaaag aattagtttc    1080
aactgaagct caaatacaga aaatgtctca agatttacag cttgaagctt taacaataca    1140
atctgaaacg cagtttctag ccggtataaa ttcacaagca gcgaatgatt gttctaaaac    1200
attgatagca gctatgttaa gccaacgtac aatgtcatta gattttgtaa ctacgaatta    1260
tatgtcactt atatctggca tgtggctatt gactgttata ccaaatgaca tgtttcttcg    1320
cgagtcgcta gtcgcatgcg aactggctat aataaatact atagtttacc cagcatttgg    1380
aatgcaaaga atgcattata gaaatggcga tcccccagact ccatttcaaa tagcagaaca    1440
acaaatacaa aatttccaag tagctaattg gttacatttt attaataata atagatttag    1500
acaagtcgtt attgatggag tgttaaatca aacacttaac gacaacatta ggaatggaca    1560
agttattaat caattaatgg aagcattaat gcaattacct agacaacaat ttccgaccat    1620
gccagttgat tataaaagat caatccaaag aggaatatta ttattgtcta acagattagg    1680
tcagttagtt gatttaacaa gattattatc atataattat gaaactctaa tggcttgtat    1740
aactatgaat atgcagcatg ttcaaactct cactaccgaa aaattacagt taacttctgt    1800
cacatcttta tgtatgttaa ttggaaatac tacagtaatt ccaagcccac aaacactatt    1860
tcactattat aacgtaaatg taaatttttca ttcaaattat aacgaacgaa ttaacgatgc    1920
tgtagctatt attacggctg ctaatagact aaacttatat cagaaaaaaa tgaaatcaat    1980
agttgaggat tttttgaaaa ggttgcaaat ttttgatgta ccacgagtac cagacgacca    2040
aatgtacagg ttgagagaca gacttagatt attgccagtt gaaagacgaa gacttgatat    2100
atttaactta atattaatga atatggagca gatcgaacga gcttcagata aaattgctca    2160
aggagtaata attgcttaca gagatatgca gctagaaaga gatgagatgt atggatttgt    2220
taacattgct aggaacctcg atggatatca acaaatcaat ttagaagagt aatgagaac    2280 tggagattat ggtcagatta ctaatatgct actaaacaac cagcctgtag ctttggttgg    2340
agcattgcca tttatgacag attcatcagt tatatcgctc attgcaaaat ggatgccac    2400 agtttttgct caaatagtta aacttagaaa agtggacact ttaaaaccaa tattatataa    2460
aataaattcc gattctaatg atttctactt agttgcaaat tatgattgga taccaacttc    2520
aaccacaaaa gtctataagc aagtaccaca accttttgat ttcaggacgt caatgcatat    2580
gttaacgtct aatttaactt ttaccgttta ctctgatttg ctatcttttg tttctgcaga    2640
cacggttgaa cctattaacg caattgcttt tgacaatatg cgcattatga acgaactgta    2700
aacgccaacc ccatttttgga gatatgccg                                     2729
```

<210> SEQ ID NO 2
<211> LENGTH: 2360
<212> TYPE: DNA
<213> ORGANISM: Human rotavirus

<400> SEQUENCE: 2

```
ggctataaaa tggcttggca catttataga caacttctca ctaattcata ctcagtagat      60
ttacatgatg aaatagaaca aattgggtca gaaaaaactc aaaacgtaac tgtaaatcca     120
ggtccgttcg ctcaaaactag gtacgctcca gttaattggg gtcatggaga gataaatgat     180
tcaaccacag tagaaccaat tttagacggt ccttatcagc ctactacatt tacaccacct     240
actgattatt ggatacttat taactcaaat acaagtggag tagtatacga gagtacgaat     300
```

```
aatagtgact tttggactgc agtcgtcgct gttgaacctc acgttaatcc agtagataga    360
caatacactg tatttggtga aaataaacaa tttaatgtaa gaaatgattc agataagtgg    420 aagttttag aaatgtttag aagcagtagt caaaatgaat tttataatag acgtacacta    480
acttctgata ctaaactcgt gggaatatta agtatggtg aaggatatg gacgtttcat    540 ggtgaaacac cgagagctac tactgatagt tcaaatacta caaatttaaa cgatatatca    600
attataatac attcagagtt ttatattatt ccaaggtctc aagaatcaa gtgtaatgag    660 tatattaata atggtttacc accaattcaa aatactagaa atgtagtacc attatcatta    720
tcatctagat ccatacagta taagagagct caagttaatg aagacattac aatttcgaaa    780
acctcattat ggaaagagat gcaatataat agggatatta taattagatt taaatttggt    840
aatagtgtta taaaactggg aggactaggt tataaatggt ccgaaatatc atttaaggca    900
gcaaactatc aatataatta tttacgtgat ggcgaacaag taactgcaca tactacttgc    960
tcagtaaatg gagtaaataa ttttagctat aacgggggac ctctacctac taattttagc   1020
atctcaagat atgaagttat caaagaaaat tcttatgtat atgtagatta ttgggatgat   1080
tcaaaagcgt ttagaaatat ggtatatgtc agatcattgg cagctaattt aaactcggtg   1140
aaatgtacag gtggaagtta cgactttagt atacctgtag gtgcatggcc agttatgaat   1200
ggaggcgctg tttcgttaca ttttgctgga gttacattat ctacgcaatt cacagatttc   1260
gtatcattga attcattacg atttagattt agtctgacag tggatgaacc atcttttca   1320 atattgagaa cacgtacagt gaatttgtac gggttaccag cagctaatcc aaataatgga   1380
aatgaatact acgaaatatc aggaaggttt tcgctcattt ctttagttcc aactaatgat   1440
gattatcaga ctccaattat gaattcagta acagtaagac aagatttaga acgtcaactt   1500
actgatttac gagaggaatt caattcatta tcacaagaaa tagctatgtc acaattaatt   1560
gatttagcat tattaccttt agatatgttt tctatgttct caggaatcaa aagtacaatt   1620
gatctgacta aatcgatggc aactagtgta atgaaaaaat ttagaaaatc aaaattagct   1680
acatcaattt cggaaatgac taattcatta tcagacgcag catcatcggc atcaagaagc   1740
gtttccatca gatcgaatat atccacaatt tcgaatttga ctaacgtttc aaatgatgta   1800
tcaaatgtga ctaatgcgtt gaatgatatt tcaacacaaa catctacaat cagtaagaaa   1860
cttagattaa gagaaatgat tactcaaact gaaggaatga gttttgatga tatttcagcg   1920
gcagtattaa aaacaaaaat agatatgtct actcaaattg gaaagtatac tttacccgac   1980
atagtcacag aggcatctga gaaatttatt ccaaaacgat catatcgaat attaaaagat   2040
gacgaagtga tggaaattaa tactgaaggg aaagtctttg catataaaat agatacactt   2100
aatgaagtac cattcgacgt aaataaattt gctgaccttg taacaaattc tccagttata   2160
tcagcaataa tagattttaa aacattaaaa aacttgaatg ataattatgg aattactcgg   2220
atagaagcac taaattttaat taaatcgaat ccaaatgtat acgtaatttt cattaaccaa   2280
aataatccaa ttataaagaa tagaattgaa cagctaattc tacaatgtaa gttgtgagaa   2340
tgcttctgga ggatgtgacc                                               2360

<210> SEQ ID NO 3
<211> LENGTH: 1356
<212> TYPE: DNA
<213> ORGANISM: Human rotavirus

<400> SEQUENCE: 3 ggctttaaa cgaagtcttc gacatggagg ttctgtactc attgtcaaaa actcttaaag     60
```

-continued

```
atgccagaga taagattgtt gaaggtacat tatattctaa tgttagcgat ctcattcagc      120
aatttaatca aatgatagta accatgaatg aaatgactt tcaaaccgga ggaattggca       180
atttacctgt tagaaactgg acattcgact ttggtctatt aggtactaca cttttaaatc      240
ttgatgccaa ctatgttgag actgcaagaa ctacgattga gtattttatt gactttattg      300
ataatgtatg tatggatgaa atggcaagag agtctcaaag aaatggagta gctccacaat      360
ctgaggcact gaggaagcta gccggtatta aatttaaaag aataaatttt aataattcat      420
cagattatat agaaaattgg aatttgcaaa atagaagaca acgtactgga tttgttttc       480 ataaacctaa tatatttcca tactcagcat catttacttt aaatagatct caaccgatgc      540
atgataattt gatgggaacc atgtggctta atgctggatc agaaattcaa gtggctggat      600
ttgactactc gtgtgctcta aatgctccag caaatattca gcagtttgaa catgttgtcc      660
agcttaggcg tgcgctaact acagctacta aactttgtt acctgatgca gaaagattta      720
gttttccaag agttattaat tcagcagatg gcgcaactac atggttcttt aatccaatta     780
ttctgagacc aaacaatgta gaggtagaat ttttacttaa tggacaaatt attaatacat      840
atcaagctag atttggcact attatcgcaa gaaattttga tacaattcgt ctatcatttc      900
aattaatgcg tccaccaaac atgacaccag ctgtaaatgc attatttccg caagcacaac      960
cttttcaaca tcatgcaaca gttggactta cgttacgtat tgattctgca gtttgtgaat     1020
cagtgcttgc ggatgcaaat gaaactttat tggcaaatgt taccgcagta cgccaagagt     1080
atgctatacc agttggccca gtattcccac caggtatgaa ttggactgag ctgattacta     1140
attattcacc atctagggaa gataatttgc aacgtgtttt tacagtagcc tctatcagaa     1200
gcatattgat taagtgagga ccagactaac catctggtat ccaatcttag ttagcatgta     1260
gctacttcaa gtcattcaga ctctgcaagt aaggacatga tttcatgttc gctacgtaga    1320
gtaactgcat gaatgatgta gtgagaggat gtgccc                              1356
```

<210> SEQ ID NO 4
<211> LENGTH: 1062
<212> TYPE: DNA
<213> ORGANISM: Human rotavirus

<400> SEQUENCE: 4

```
ggctttaaaa gcgagaattt ccgtctggct aacggttagc tccttttgat gtatggtatt       60
gaatatacca caattctaat cttttctgata tcaatcattc tacttaacta tatattaaaa      120
tcagtgaccc gaataatgga ctacattata tatagatttt tgttaatttc tgtagcatta      180
tttgccttga ctagagctca gaactatgga cttaatatac caataacagg atcaatggac      240
actgtatata tcaactctac tcaagaagga atgtttctaa catccacatt atgtttgtat      300
tatccaactg aagcaagagc tcaaatcagt gatggtgaat ggaaagactc attatcacaa      360
atgtttctta caaaaggttg gccaacagga tcagtctatt ttaaagagta ctcaaatatt      420
gttgattttt ccgttgaccc acaattatat tgtgattata acttagtact aatgaagtat      480
gatcaaaatc ttgaactaga tatgtcagaa ttagccgatt tgatattgaa tgaatggtta      540
tgtaatccaa tggatgtaac attatatatt atcaacaat cgggagaatc aaataagtgg       600
atatcgatgg gatcatcatg tactgtaaag gtgtgtccgt tgaatacaca aacgttagga      660
ataggttgtc aaacaacgaa tgtagactca tttgaaacag ttgctgaaaa tgaaaaattg      720
gctatagtgg atgtcgttga tggaataaat cataaaataa atttgacaac tacgacatgt      780
```

-continued

```
actattcgaa attgtaagaa gttaggtcca agagagaatg tagctgtcat acaagttggt    840
ggctctaata tattagacat aacagcggat ccaacgacta atccacaaat tgagagaatg    900
atgagagtga attggaaaag atggtggcaa gtattttata ctatagtaga ttatattaat    960
cagattgtac aggttatgtc caaaagatca agatcattaa attctgctgc gttttattat   1020
agagtataga tatatcttag attagagttg tatgatgtga cc                      1062
```

<210> SEQ ID NO 5
<211> LENGTH: 1062
<212> TYPE: DNA
<213> ORGANISM: Human rotavirus

<400> SEQUENCE: 5

```
ggctttaaaa gcgagaattt ccgtctggct agcggttagc tctttttaat gtatggtatt     60
gaatatacca caattctgac cattttgata tttatcatat tattgaatta tatattaaaa    120
actataacta acacgttgga ctatataatt tttaggcttt tactactcat cgctctgatg    180
tcaccatttg tgaggacgca aaattatggt atgtatttac caataacagg atcaccagac    240
gctgtataca caaattcaac tagtggagaa tcatttctaa cttcaacgct atgtttatac    300
tatccaacag aagctaaaaa tgagatttca gataatgaat gggaaaatac tctatcgcaa    360
ttatttttaa ctaaaggatg gccgactgga tcagtttatt ttaaagacta caatgatatt    420
actacatttt ctatgaatcc acaactatat tgtgattata atgtagtatt aatgagatat    480
gataatacat ctgaattaga tgcatcggag ttagcagatc ttatattgaa cgaatggctg    540
tgcaatccta tggatatatc actttactat tatcaacaaa atagcgaatc aaataaatgg    600
atatcaatgg gaacagactg tacggtaaaa gtttgtccac tcaatacaca aactttagaa    660
attgaatgca aaaatacgaa cgtggataca tttgagattg ttgcctcgtc tgaaaaattg    720
gtaattactg atgttgtaaa tggtgttaat cataaaataa atatttcaat aagtacgtgt    780
actatacgta attgtaataa actaggacca cgagaaaatg ttgctataat tcaagttggt    840
ggaccgaacg cactagatat cactgctgat ccaacaacag ttccacaggt tcaaagaatc    900
atgcgagtaa attggaaaaa atggtggcaa gtgttttata cagtagttga ctatattaac    960
caaattatac aagttatgtc caaacggtca agatcattag acacagctgc tttttattat   1020
agaatttaga tatagctttg gttagagttg tatgatgtga cc                      1062
```

<210> SEQ ID NO 6
<211> LENGTH: 1062
<212> TYPE: DNA
<213> ORGANISM: Human rotavirus

<400> SEQUENCE: 6

```
ggctttaaaa gagagaattt ccgtctggct agcggttagc tccttttaat gtatggtatt     60
gaatatacca cagttttaac ctttttgata tcagttatat tgttgaatta cgtactcaaa    120
tccttaacta gaataatgga ctttattatt tacagatttc ttttgattat agttatatta    180
tcaccattcc ttaatgcaca aaattatgga ataaatcttc cgattactgg ctcaatggac    240
acaccatata tgaactcaac acgagaggaa gtattcctaa cttcgacttt atgtttgtat    300
tacccaactg aagcagcaac agaaataaat gataattcat ggaaggatac actttctcag    360
ctatttttaa tcaaaggatg gccaacagga tctgtttatt ttaaagatta tactgatatt    420
gcctcgtttt cagttgatcc acaactgtac tgtgattata atttggtatt aatgaaatac    480
gacgctacac tgcaactgga catgtccgaa ctagcagatt tgttacttaa tgaatggtta    540
```

```
tgtaatccta tggatattac tttgtattat tatcaacaaa ctgatgaggc aaataagtgg    600
atttcaatgg gatcatcttg tactataaag gtatgtccac taaatacgca aacattagga    660
attgggtgcc taacaactga tacaaacacg tttgaagaag ttgcaacagc tgaaaaatta    720
gtgattactg acgttgtaga tggcgtcaat cataaattga acgtgacgac aaacacttgt    780
acgattagaa attgtaaaaa attaggacca agggaaaacg tagcagttat acaggttggt    840
ggcccagatg tacttgacat aacagctgat ccaacgacaa tgccacaaac agaaagaatg    900
atgcgagtga attggaagaa atggtggcaa gtgttttata caatagttga ctacgtgaat    960
caaattgtgc aagcgatgtc caaaagatcg agatcattaa attctgctgc attttactac   1020
agggtatagg tatagcttag gttagaattg tatgatgtga cc                      1062

<210> SEQ ID NO 7
<211> LENGTH: 1062
<212> TYPE: DNA
<213> ORGANISM: Human rotavirus

<400> SEQUENCE: 7
ggctttaaaa gcgcgaattt ctgtttggct agcagatagc tccttttaat gtatggtatt     60 gaataccca cagttctatt ttatttgata tcgttcgttc ttgtgagtta tattctgaaa    120
actataataa agataatgga ctatattatt tatagaataa catttgtaat tgtagtatta    180
tcagtattat cgaatgcaca aaattatgga ataaatttgc caattactgg atctatggat    240
acagcatatg ctaactcaac acaagacaat aattttttat cttcaacttt atgtctatat    300
tatccatcag aagctccaac tcaaattagt gacactgaat ggaaagatac actatctcag    360 ttgttttaa ccaaaggatg gccgacaggt tcagtttatt ttaatgaata ttcaaacgtt    420
ttagaatttt ccatcgaacc aaagttatac tgtgattata atgttgtgct gattaagttc    480
gcttctggtg aggaattgga catatctgaa ttagctgatc taatattgaa tgagtggtta    540
tgtaatccaa tggatataac attatattat tatcagcaaa ctggagaggc gaataaatgg    600
atatcaatgg gatcatcatg taccgttaaa gtgtgtccat taaatactca gacattagga    660
attggatgtc aaacgacaaa tacagctact tttgaaacag ttgctgatag cgaaaaattg    720
gcaataattg atgttgtcga cagtgtaaat cataaattag atgttacatc tactacatgt    780
acaatacgga attgtaataa actaggaccg agagaaaatg tggccataat acaggttggc    840
ggttctaata tattagatat aacagctgat cccacaactt ctccacaaac agaacgaatg    900
atgcgcgtga attggaaaaa atggtggcaa gtattctata ctgtagttga ttacattaat    960
cagatagtac aagtaatgtc caaaagatcg agatcgttag attcgtcatc tttctattat   1020
agagtgtaga tatatcctaa aatagagttg tatgatgtga cc                      1062
```